(12) United States Patent
Van Rheenen et al.

(10) Patent No.: US 6,812,358 B2
(45) Date of Patent: Nov. 2, 2004

(54) PROCESS FOR MAKING ESTRA-4,9(10)-DIENE STEROIDS

(75) Inventors: Verlan H. Van Rheenen, Portage, MI (US); Edward J. Hessler, Kalamazoo, MI (US)

(73) Assignee: Bridge Organics Co., Vicksburg, MI (US)

( * ) Notice: Subject to any disclaimer, the term of this patent is extended or adjusted under 35 U.S.C. 154(b) by 33 days.

(21) Appl. No.: 10/163,727

(22) Filed: Jun. 6, 2002

(65) Prior Publication Data

US 2003/0004333 A1 Jan. 2, 2003

Related U.S. Application Data

(60) Provisional application No. 60/296,999, filed on Jun. 8, 2001.

(51) Int. Cl.[7] .......................... C07J 1/00; A61K 31/56; A61K 31/58; C07D 223/14
(52) U.S. Cl. ...................... 552/623; 540/543; 514/172; 514/177; 514/169
(58) Field of Search .......................... 540/543; 552/623, 552/626, 556; 514/172, 177, 169

(56) References Cited

U.S. PATENT DOCUMENTS 3,211,719 A * 10/1965 Wartburger .............. 260/210.5

OTHER PUBLICATIONS

Gardi et al. (DN 60:52915, HCAPLUS, abstract of Gazz. Chim. Ital. (1963), 93(11), 1503–19).*

R. Bucourt et al., J. Biol. Chem. vol. 253, pp. 8221–8228 (1978).

Templeton et al., J. Chem. Soc., Perkin Trans. I, pp. 1149–1158 (1994).

Zderic et al., J. Am. Chem. Soc., vol. 81, pp. 3120–3124 (1959).

M. Rosenberger et al., J. Org. Chem., vol. 43, pp. 1550–1555 (1978).

R.M. Weier et al., J. Med. Chem., vol. 19, pp. 975–977 (1976).

* cited by examiner

Primary Examiner—Sabiha Qazi
(74) Attorney, Agent, or Firm—MacMillan, Sobanski & Todd, LLC

(57) ABSTRACT

A novel process for making estra-4,9(10)-diene-3,17-dione steroids from readily available 19-nor-androst-4-ene-3-one steroids by a straightforward three-step process. Products of this process are important intermediates in the preparation of biologically active substances.

5 Claims, No Drawings

PROCESS FOR MAKING ESTRA-4,9(10)-DIENE STEROIDS

CROSS-REFERENCE TO RELATED APPLICATION

This application claims the benefit of U.S. provisional application Ser. No. 60/296,999, filed Jun. 8, 2001.

BACKGROUND OF THE INVENTION

Estra-3-keto-4,9(10)-diene steroids (all steroids herein have the natural stereochemistry unless otherwise defined), the products of this invention, are known valuable intermediates to biologically active substances (see G. Teutsch in *Adrenal Steroid Antagonism*, 5d. M. K. Agarwal, W. deGruyter and G. Berlin, 1984, pp. 43–75). U.S. Pat. No. 3,461,118 prepares this 3-keto-4,9(10)-diene structural feature from a 3-keto-Δ5(10)-steroid by a process using bromine and pyridine. In the patent, the 3-keto-Δ5(10)-steroid is produced by hydrolysis of the corresponding ketal, but it also can be made by many chemical routes (see CAN 69:77598; NL 6608779), most prominent among them by a Birch reduction of the 3-protected estrone followed by hydrolysis (see CAN 66:65723, NL 6607002).

In French Patent 1,568,711, this same 3-keto starting material, estra-5(10)-ene-3-one steroid, is converted into the subject estra-3-keto-4,9(10)-diene steroids, by a chlorination or iodination process as well as a process of epoxidation, epoxide opening under strongly basic conditions (i.e. potassium hydroxide in refluxing methanol), to produce the 10-hydroxy-estra-4-ene-3,17-dione which is an intermediate of the present invention. This intermediate is carried on by methane sulfonate ester formation followed by treatment with sodium acetate in acetic acid, a process very different from the present invention, and using a starting material different from the present invention.

SUMMARY OF THE INVENTION

The following Chart A illustrates the process of the invention, including the steroid structures and functional group variations. Chart B illustrates steroid structures related to those shown in Chart A.

Disclosed are steroidal epoxides (II) of estra-5(10)-ene-3,17-dione-3,17-bis-ketals (I), specifically 7α-methyl-5(10)-oxido-estra-3,17-dione steroids (IIA), 10-hydroxy-estra-4-ene-3-one steroids (III), and 5,10-dihydroxy-estra-3-one steroids (IV). Also disclosed is a process for preparation of a steroid having the 4,9(10)-diene-3-one structure (VA) by contacting a 10-hydroxy-4-ene-3-ketosteroid (IIIA) and/or a 5,10-dihydroxy-3-ketosteroid (IVA) with concentrated sulfuric acid or moderated sulfuric acid. Further disclosed is a process for preparing estra-3-keto-4,9(10)-diene steroids (V) starting with estra-5(10)-ene-3,17-dione-3,17-bis-ketals (I), derivable from 19-norandrost-4-ene-3-one steroids, comprising contacting (a) Δ5(10)-bis-ketals (I) with an epoxidizing agent to prepare epoxides (II), (b) contacting the epoxides (II) with dilute acid to produce hydroxy compounds (III) and (IV), and (c) contacting the hydroxy compounds (III) and (IV) with concentrated sulfuric acid. Also disclosed is a process for preparation of steroidal estra-4,9(10)-diene-3,17-diones of structure (V) by treatment of steroidal estra-5(10),9(11)-diene-3,17-diones of structure (VI) with concentrated mineral acid.

CHART A

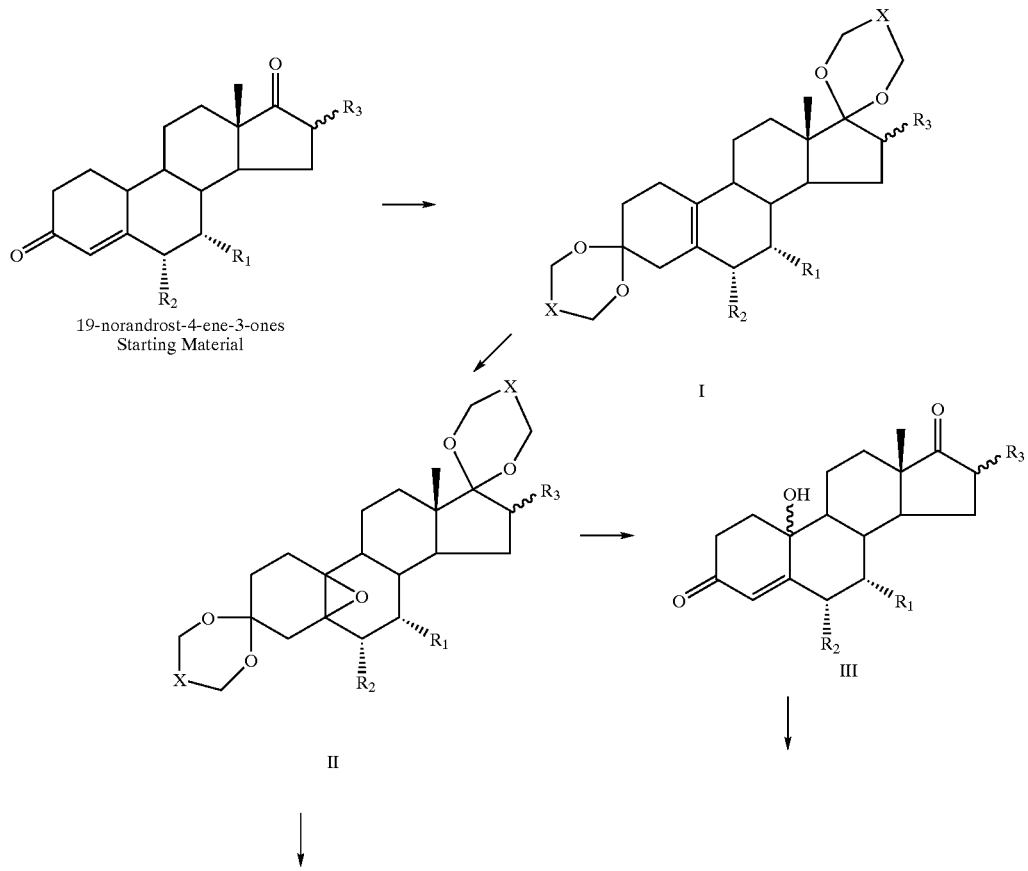

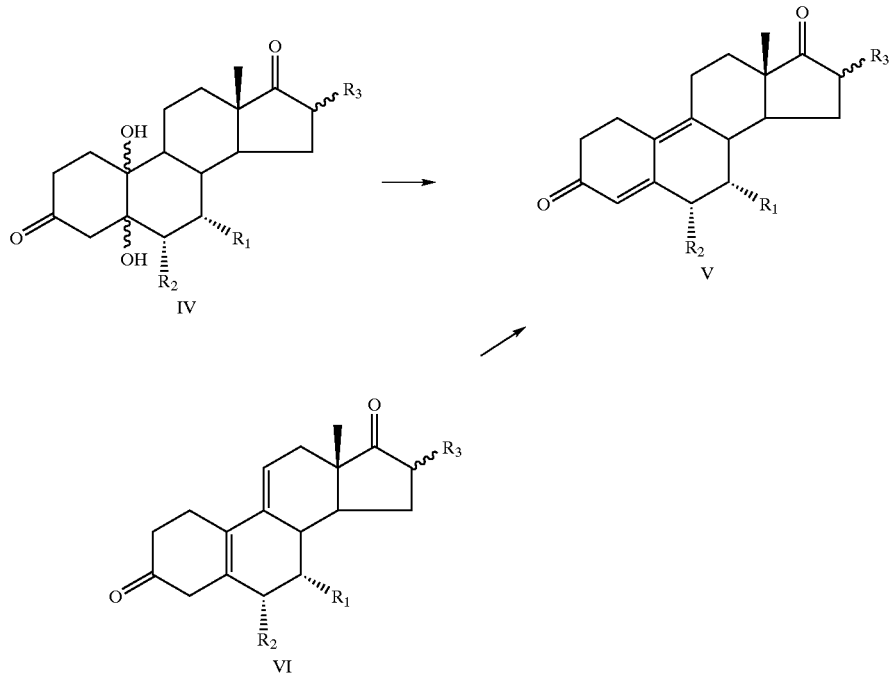

$R_1$ = CH$_3$, H, COOCH$_3$
$R_2$ = CH$_3$, F, H
$R_3$ = CH$_3$, OH, F, H
X = nothing, C(CH$_3$)$_2$, CH$_2$
⋯⋯ = alpha orientation
▬ = beta orientation
∼∼∼ = alpha or beta orientation

CHART B

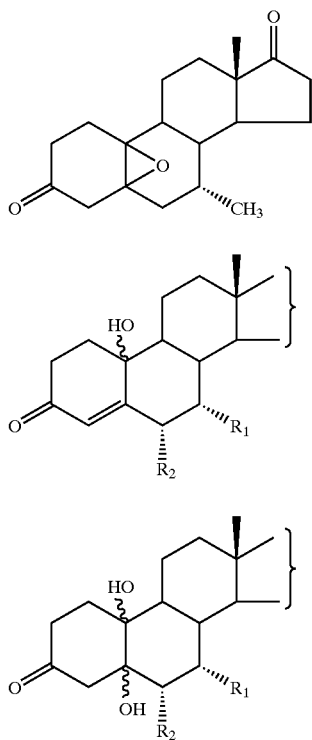

$R_1$=CH$_3$, H, COOCH$_3$
$R_2$=CH$_3$, F, H

⋯⋯=alpha orientation
▬=beta orientation
∼∼∼=alpha or beta orientation

DETAILED DESCRIPTION OF THE PREFERRED EMBODIMENTS

The estra-5(10)-ene-3,17-dione-3,17-bis-ketals (I), the starting materials for the process of the invention, are known in the art: for examples see John F. Templeton et al., J. Chem. Soc., Perkin Trans. 1 (1994), (9), 1149-58; and C. Djerassi, et al., J. Am. Chem. Soc., vol. 81, p 3120 (1959). As shown in Chart A, these Δ5(10)-bis-ketals (I) are typically derived from the readily available 19-nor-androst-4-ene-3-one steroids by standard ketalization methods. Of the many ketals possible, it is preferred that the ketal be derived from ethylene glycol or neopentyl glycol, the latter most preferred.

The structure and functional group variations of the Δ5(10)-bis-ketals (I) are shown in the chart. Some nonlimiting examples of preferred Δ5(10)-bis-ketals (I) for use in the invention include 7α-methyl-estra-5(10)-ene-3,17-dione-3,17-bis-ethylene glycol ketal, 7α-methyl-estra-5 (10)-ene-3,17-dione-3,17-bis-neopentyl glycol ketal, and estra-5(10)-ene-3,17-dione-3,17-bis-neopentyl glycol ketal.

As shown in Chart A, the estra-5(10)-ene-3,17-dione-3, 17-bis-ketals (I) are epoxidized to produce bis ketal-5(10)-epoxide products (II). Epoxidation of olefins is a standard reaction in organic chemistry (see Fieser and Fieser, *Reagents for Organic Synthesis*, Vol. 1–20, John Wiley & Sons, Inc., N.Y. 1967–2000), but epoxidation of the olefin in Δ5(10)-bis-ketals (I) has not been reported, nor have the requisite epoxide products (II) been reported. Many epoxidizing agents may be used, but preferred is the use of m-chloroperbenzoic acid or peracetic acid in solvents that do not react with peracids, such as methylene chloride. The epoxidizing reaction can be conducted under a wide range of temperatures, but preferred is 0° C. to ambient. The bis-ketal-5(10)-epoxide products (II) are isolated in high conversion by a standard workup, and generally need no further purification by crystallization or chromatography.

The structure and functional group variations of the bis-ketal-5(10)-epoxides (II) are shown in the chart. In some preferred embodiments of the structure, $X=C(CH_3)_2$ and $R_1=CH_3$, $R_2=R_3=H$. Some nonlimiting examples of preferred bis-ketal-5(10)-epoxides (II) for use in the invention include 7α-methyl-5(10)-oxido-estra-3,17-dione-3,17-bis-ethylene glycol ketal, 7α-methyl-5(10)-oxido-estra-3,17-dione-3,17-bis-neopentyl glycol ketal, and 5(10)-oxido-estra-3,17-dione-3,17-bis-neopentyl glycol ketal.

As shown in Chart B, 7α-methyl-5(10)-oxido-estra-3,17-dione steroids (IIA) is the product from epoxidation of the Δ5(10)-bis-ketals (I) ($R_1=Ch_3$, $R_2=R_3=H$) to the bis-ketal-5(10)-epoxide products (II) ($R_1=Ch_3$, $R_2=R_3=H$) followed by mild acid hydrolysis.

Referring again to Chart A, in a second step of the process, the bis-ketal-5(10)-epoxides (II) are contacted under dilute acidic conditions to effect both ketal hydrolysis and epoxide opening to give mixtures of 10-hydroxy-estra-4-ene-3-ones (III) and 5,10-dihydroxy-estra-3-ones (IV). The ratio of these monohydroxy and dihydroxy products is not important for the purposes of this invention because both are efficiently converted into the estra-4,9(10)-diene-3-ones (V), the end product of this invention. Many acids and many solvents with water may be used to effect conversion of (II) to (III) and (IV), but preferred are dilute aqueous mineral acids in water miscible solvents such as acetone or tetrahydrofuran. More preferred is contact of the epoxy ketals (II) with ~0.5 M hydrochloric acid in acetone at ambient temperature. The reaction products (III) and (IV) may be isolated by extractive procedures or preferably as a solid by evaporation of the volatile solvent.

The structures and functional group variations of the reaction products (III) and (IV) are shown in the chart. In some preferred embodiments of compounds (III), $R_1=CH_3$, $R_2=R_3=H$; or $R_1=R_2=R_3=H$. Some nonlimiting examples of preferred 10-hydroxy-estra-4-ene-3-ones (III) for use in the invention include 10-hydroxy-7α-methyl-estra-4-ene-3,17-dione, 10-hydroxy-6α-methyl-estra-4-ene-3,17-dione, and 10-hydroxy-estra-4-ene-3,17-dione. In some preferred embodiments of compounds (IV), $R_1=CH_3$, $R_2=R_3=H$; or $R_1=R_2=R_3=H$. Some nonlimiting examples of preferred 5,10-dihydroxy-estra-3-ones (IV) for use in the invention include 5,10-dihydroxy-7α-methyl-estra-3,17-dione, 5,10-dihydroxy-6α-methyl-estra-3,17-dione, and 5,10-dihydroxy-estra-3,17-dione.

In the final step of the process (Chart A), the 10-hydroxy-estra-4-ene-3-ones (III) and 5,10-dihydroxy-estra-3-ones (IV) are converted by acidic dehydration to the product of this invention, estra-3-keto-4,9(10)-diene steroids (V). This conversion is surprisingly and unexpectedly specific to concentrated sulfuric acid and slightly moderated forms of sulfuric acid. Other readily available concentrated acids do not efficiently make this conversion. Those acids which give none or poor conversions to the target estra-3-keto-4,9(10)-diene steroids (V) of this invention include phosphoric acid, formic acid, trifluoroacetic acid, acetic acid, and methane-sulfonic acid.

By "concentrated" sulfuric acid is meant sulfuric acid at a concentration of at least 95%, and typically 95–99%. The sulfuric acid can be moderated by admixture with water, with the water being present in an amount of up to 5% by volume of the moderated acid. The sulfuric acid can also be moderated by admixture with a second acid, such as one of the abovementioned acids, or mixtures of different acids. The second acid is present in an amount of up to 30% by volume of the moderated acid. Preferred is concentrated phosphoric acid (concentration of at least 85%), preferably at a ratio of about ⅙ of volume of sulfuric acid. The speed and reactivity of the reaction can be adjusted to the requirements of individual substrates by adjusting this ratio, the greater reactivity with the lowest amount of phosphoric acid. It is convenient to dissolve the hydroxy compounds (III) and (IV) in an inert solvent such as methylene chloride before adding them to the concentrated or moderated sulfuric acid. The hydroxy compounds may also be added directly as a solid to the concentrated or moderated sulfuric acid. The preferred reaction temperature is ambient to 0° C., although other temperatures may be used. The estra-3-keto-4,9(10)-diene steroid product (V) is conveniently isolated from the sulfuric acid reaction by adding ice, partial neutralization, extraction with acid stable, water immiscible solvent (preferably methylene chloride), evaporation and crystallization.

The structure and functional group variations of the estra-3-keto-4,9(10)-diene steroids (V) are shown in the chart. Some nonlimiting examples of preferred products (V) of the invention include 7α-methyl-estra-4,9(10)-diene-3,17-dione, 6α-methyl-estra-4,9(10)-diene-3,17-dione, 16β-methyl-estra-4,9(10)-diene-3,17-dione, and estra-4,9(10)-diene-3,17-dione. In one embodiment of the overall process of the invention, 7α-methyl-estra-4,9(10)-diene-3,17-dione (V) is prepared from 7α-methyl-estra-5(10)-ene-3,17-dione-3,17-bis-ethylene glycol ketal (I) or 7α-methyl-estra-5(10)-ene-3,17-dione-3,17-bis-neopentyl glycolketal (I). In another embodiment, estra-4,9(10)-diene-3,17-dione (V) is prepared from estra-5(10)-ene-3,17-dione-3,17-bis-ethylene glycol ketal (I) or estra-5(10)-ene-3,17-dione-3,17-bis-neopentyl glycolketal (I).

More generally, the acidic dehydration process described above is useful for converting 10-hydroxy-4-ene-3-ketosteroids (IIIA), 5,10-dihydroxy-3-ketosteroids (IVA), and mixtures of (IIIA) and (IVA), into steroids having the 4,9(10)-diene-3-one structure (VA) (all shown in Chart B). In one preferred embodiment of the process, estra-4,9(10)-diene-3,17-dione (VA) is prepared from 10-hydroxy-estra-4-ene-3,17-dione (IIIA), 5,10-dihydroxy-estra-3,17-dione (IVA), or mixtures thereof. In another embodiment of the process, 7α-methyl-estra-4,9(10)-diene-3,17-dione (VA) is prepared from 10-hydroxy-7α-methyl-estra-4-ene-3,17-dione (IIIA), 5,10-dihydroxy-estra-3,17-dione (IVA), or mixtures thereof.

As further shown in Chart A, dienes of structure (VI) are intermediates and by-products from reaction of (III) and/or (IV) with sulfuric acid and moderated sulfuric acid. Dienes of structure (VI) ($R_1=R_2=R_3=H$ or $R_1=CH_3$, $R_2=R_3=H$) are known in the literature: see U.S. Pat. No. 3,691,215 and M. Rosenberger et al., *J. Org. Chem.* 43, 1550 (1978) for conversion of (VI) into (V). In another embodiment of the present invention, concentrated mineral acid (at least 85% concentration) is used to effectively produce the product, estra-3-keto-4,9(10)-diene steroids (V), by contact with the estra-3-keto-5(10),9(11)-diene steroids of structure (VI). Any suitable concentrated mineral acid or mixtures thereof can be used, such as phosphoric and/or sulfuric acid. Mineral acid high in phosphoric acid is preferred, and most preferred is concentrated phosphoric acid.

EXAMPLES

Example 1

7α-methyl-5(10)-oxido-estra-3,17-dione-3,17-bis-ethylene glycol ketal (II)

To a stirred solution of 20 Mmoles of 7α-methyl-estra-5 (10)-ene-3,17-dione-3,17-bis-ethylene glycol ketal (I) (see Example 7) and 3 g of solid potassium carbonate in 20 ml of methylene chloride at 5° C. was added dropwise 8 g of m-chloroperbenzoic acid in 40 ml of methylene chloride over one hour. This exothermic reaction became a thick slurry. The reaction was judged to be complete by TLC (¼ ethyl acetate/hexane, Rf 0.8) after one hour. Water was added and the phases separated. The organic phase was washed with 0.5 M sodium bisulfite, brine, filtered through celite, and dried over sodium sulfate. The solvent was evaporated under vacuum leaving a colorless oil used as such in the next step. NMR($CDCl_3$); 0.86 ppm (3H, s), 0.84 ppm (3H, d), 3.9 ppm (4H, m).

Example 2

10-hydroxy-7α-methyl-estra-4-ene-3,17-dione (III) and 5,10-dihydroxy-7α-methyl-estra-3,17-dione (IV)

To 20 Mmoles of 7α-methyl-5(10)-oxido-estra-3,17-dione-3,17-bis-ethylene glycol ketal (II) from example 1 in 40 ml of acetone was added 20 ml of water and 5 ml of 1 N hydrochloric acid. This initially heterogeneous mixture was stirred at ambient temperature for ~60 hrs. at which time it was judged complete by TLC (¼ ethyl acetate/hexane, Rf 0.2). The reaction was neutralized with 1M potassium carbonate and the acetone was mostly removed by evaporation under vacuum. The aqueous suspension obtained was extracted with methylene chloride, the organic phases washed with brine, dried over sodium sulfate, and evaporated to produce a solid mass. NMR ($CDCl_3$) showed two doublets at 0.85 and 1.12 ppm in a 3:1 ratio; the doublet at 0.85 is the 7α-methyl group in the enone (III), and the doublet at 1.12 is the 7α-methyl group of the dihydroxy compound (IV).

Example 3

7α-methyl-estra-4,9(10)-diene-3,17-dione (V)

To 15 ml of concentrated sulfuric acid (98%) cooled to ~5° C. was added dropwise ~20 Mm of a mixture containing 10-hydroxy-7α-methyl-estra-4-ene-3,17-dione (III) and 5,10-dihydroxy-7α-methyl-estra-3,17-dione (IV) from example 2 dissolved in 15 ml of methylene chloride. About 20 minutes after the addition was complete, TLC (¼ ethyl acetate/hexane, Rf 0.4) showed that the reaction was complete. The deep red reaction mixture was poured over ice, washed in with methylene chloride, partially neutralized with potassium carbonate, and the phases separated. The organic phase was washed with dilute aqueous potassium carbonate, brine, and dried over sodium sulfate, and concentrated under vacuum to a solid product. This material was column chromatographed on 150 g of silica gel with gradient elution from ⅓ to ¼ ethyl acetate/hexane. Fractions 6–9 were combined to give a solid which was recrystallized from ethyl acetate to provide the title product. Mp 208–209° C.

Example 4

Isolation of 10-hydroxy-7α-methyl-estra-4-ene-3, 17-dione (III) and 5,10-dihydroxy-7α-methyl-estra-3,17-dione (IV)

Material prepared following the general procedure of examples 1 and 2 was column chromatographed on silica gel using gradient elution from 5% to 60% methyl t-butyl ether in methylene chloride. Fractions 28–30 were combined and condensed to crystalline 10-hydroxy-7α-methyl-estra-4-ene-3,17-dione (III): mp 204.8–209.4° C.

NMR($CDCl_3$); 0.86 ppm (3H, d, J=7 hz), 0.98 ppm (3H, s), 3.0 ppm (1H, m), 5.80 ppm (1H, s).

Fraction 37 gave crystalline 5,10-dihydroxy-7α-methyl-estra-3,17-dione (IV) from methylene chloride: mp 240.8° C.

NMR($CDCl_3$); 0.96 ppm (3H, s), 1.12 ppm (3H, d, J=7hz), 2.99 ppm (1H,d).

Example 5

7α-methyl-estra-4,9(10)-diene-3,17-dione (V) from 10-hydroxy-7α-methyl-estra-4-ene-3,17-dione (III)

To 12 ml of concentrated sulfuric acid cooled to 0° C. was added dropwise 6.9 g of 10-hydroxy-7α-methyl-estra-4-ene-3,17-dione (III) in 17 ml of methylene chloride. After addition the reaction was allowed to slowly warm to 13° C. After one hour the reaction mixture was poured onto ice, partly neutralized with solid potassium carbonate, and extracted with methylene chloride. The combined aqueous phases were washed to neutrality with pH 7 buffer, dried by passing through a bed of sodium sulfate and silica gel, and evaporated to a solid mass. Recrystallization from ethyl acetate gave the title product.

Mp 203.7–208° C.

Rotation –173 degrees

Example 6

7α-methyl-estra-4,9(10)-diene-3,17-dione (V) from 5,10-dihydroxy-7α-methyl-estra-3,17-dione (IV)

To 1.5 ml of concentrated sulfuric acid and 0.25 ml of 85% phosphoric acid cooled to ice bath temperature was added portionwise a slurry of 1.0 g of 5,10-dihydroxy-7α-methyl-estra-3,17-dione (IV) in 2 ml of methylene chloride. On warming to ambient temperature the reaction was judged complete by TLC (¼ ethyl acetate/hexane). The red two phase reaction mixture was poured into buffered ice water, partly neutralized with potassium carbonate, extracted into methylene chloride, washed with dilute potassium carbonate and water, dried over sodium sulfate, and concentrated to give the title product.

Mp 208–209° C.

Example 7

7α-methyl-estra-5(10)-ene-3,17-dione-3,17-bis-ethylene glycol ketal (I)

This and other 3,17-bis-ketals (I) of 19-nor-androst-4-ene-3,17-dione, and derivatives, were prepared following the general procedures of Djerassi, et al., J. Am. Chem. Soc., vol. 81, p 3120 (1959) and Templeton, et al., J. Chem. Soc., Perkin Trans. I (1994), p 1149, making non critical variations as required.

Example 8

7α-methyl-5(10)-oxido-estra-3,17-dione-3,17-bis-neopentyl glycol ketal (II)

To a solution of 5.58 g of 7α-methyl-estra-5(10)-ene-3, 17-dione-3,17-bis-neopentyl glycol ketal (I) in 50 ml of methylene chloride was added portionwise 3.6 g of m-chloro perbenzoic acid. The reaction was complete 10 minutes after the last addition. pH 7 aqueous buffer and ~10 ml of 0.5 M sodium bisulfite was added and the slurry filtered. The two-phase filtrate was separated, the aqueous phase washed with methylene chloride, the combined organic phases washed with potassium bicarbonate, and dried over sodium sulfate. Concentration under vacuum gave the title compound as a colorless oil, which was crystallized from methylene chloride/heptane, m.p. 170–171° C. NMR (CDCl$_3$); 0.70 ppm (3H,s), 0.80 ppm (3H,s), 0.79 ppm (3H, d, J=6 hz), 0.91 ppm (3H, s), 0.97 ppm (3H, s), 1.12 ppm (3H, s), 3.45 ppm (8H, m).

Example 9

10-hydroxy-7α-methyl-estra-4-ene-3,17-dione (III) and 5,10-dihydroxy-7α-methyl-estra-3,17-dione (IV)

The 7α-methyl-5(10)-oxido-estra-3,17-dione-3,17-bis-neopentyl glycol ketal (II) from the previous example was placed in 50 ml of acetone, 12.5 ml of water, and 12.5 ml of 1N hydrochloric acid, and stirred ~20 hours at ambient temperature after which the reaction was judged complete by TLC. The slurry resulting from slow addition of 50 ml of water was filtered and dried, giving the title products.

Example 10

7α-methyl-estra-4,9(10)-diene-3,17-dione (V)

To 4.5 ml of concentrated (98%) sulfuric acid and 0.75 ml of 85% phosphoric acid cooled to ice bath temperature was added 2.9 g of the 10-hydroxy-7α-methyl-estra-4-ene-3,17-dione (III) and 5,10-dihydroxy-7α-methyl-estra-3,17-dione (IV) crude mixture dissolved in 6 ml of methylene chloride. The resulting reaction was complete in one hour, at which time the red reaction mixture was added to ice, partly neutralized with potassium carbonate and extracted with methylene chloride. The combined organic phases were washed with pH 7 buffer, dried over sodium sulfate and evaporated to a solid. The solid was crystallized from ethyl acetate to give the title compound.

Example 11

10-hydroxy-6α-methyl-estra-4-ene-3,17-dione (III) and 5,10-dihydroxy-6α-methyl-estra-3,17-dione (IV)

The starting material for this sequence, 6α-methyl-estra-4-ene-3,17-dione is prepared from commercial 19-nor-androst-4-ene-3,17-dione by the methodology disclosed in U.S. Pat. Nos. 3,823,138, 3,642,840, and 3,679,715. The bis-ketals of 6α-methyl-estra-4-ene-3,17-dione (I) are prepared as described in Example 7. Following the general procedures given in examples 1, 2 and/or 8, 9 above and making non-critical variations, the bis ketals of 6α-methyl-estra-4-ene-3,17-dione (I) are converted into the title compounds.

Example 12

6α-methyl-estra-4,9(10)-diene-3,17-dione (V)

Following the general procedures of example 3 and/or 10 above and making non-critical variations, the products of example 11 are converted into the title compound.

Example 13

16β-methyl-estra-4,9(10)-diene-3,17-dione (V)

The starting material, 16β-methyl-estra-4-ene-3,17-dione is prepared from commercial 19-nor-androst-4-ene-3,17-dione by the methodology disclosed in U.S. Pat. No. 4,451,404. The requisite ketals, 16β-methyl-estra-5(10)-ene-3,17-dione-3,17-bis-ethylene glycol ketals (I) are prepared by the procedures in example 7. Using the general procedures given in examples 1, 2, 3 and/or 8, 9, 10 above and making non-critical variations, the 16β-methyl-estra-5(10)-ene-3, 17-dione-3,17-bis-ethylene glycol ketals (I) are converted into the title compound.

Example 14

7α-methyl-19-nor-androst-4-ene-3,17-dione (starting material)

This starting material for ketal preparation in example 7 above is prepared by the general methodology described by R. Bucourt, et al. in J. Biol. Chem. Vol. 253, pp. 8221–8228 (1978) and making non-critical variations.

Example 15

7α-carbomethoxy-19-nor-androst-4-ene-3,17-dione (starting material)

The title compound is prepared by hydrocyanation and methanolysis of 19-nor-androst-4,6-diene-3,17-dione. The general procedures for hydrocyanation and methanolysis are given in U.S. Pat. Nos. 3,890,304 and 3,773,758, R. M. Wier, et al., J. Med. Chem. 19, p. 975 (1976), and application WO 97-US23090 19971211.

Example 16

7α-carbomethoxy-estra-4,9(10)-diene-3,17-dione (V)

The 7α-methyl-estra-5(10)-ene-3,17-dione-3,17-bis-ethylene glycol ketals (I) are prepared as described in example 7. The title compound is prepared using the general procedures given in examples 1, 2, 3 and 8, 9, 10 above.

Example 17

5(10)-oxido-estra-3,17-dione-3,17-bis-neopentyl glycol ketal (II)

To a stirred solution of 324.2 Mmoles of estra-5(10)-ene-3,17-dione-3,17-bis-neopentyl glycol ketal (I) and 1440 ml of dichloromethane stirring at 5° C. was added solid 3-chloroperbenzoic acid (89.0 g) in 9.0 gram portions (1 portion every 5 minutes). One hour after the acid was added the reaction was judged to be complete by TLC (⅓ hexane/ethyl acetate). The organic phase was washed with 430 ml of water containing 7.5 grams of sodium bisulfite, then 1300 ml of water and 60 grams of potassium carbonate. The aqueous phases were reextracted with 2×300 ml of dichloromethane. The organic phases were combined, dried over magnesium sulfate, filtered and concentrated under vacuum to an oil. This oil was used directly in the next step.

Example 18

10-hydroxy-estra-4-ene-3,17-dione (III) and 5,10-dihydroxy-estra-3,17-dione (IV)

To the above oil (II) was added 1200 ml of acetone and 360 ml of water and 20 ml of concentrated hydrochloric acid. The solution was stirred overnight at room temperature, and the reaction was shown to be complete by the absence of starting material and the presence of only 2 components. The solution was diluted with 20% potassium carbonate (100 ml) and the acetone was removed by vacuum concentration. Upon cooling to 2° C. a first crystal crop was obtained. This was filtered, washed (2×200 ml of water), and dried to give a first crop which was shown by NMR to be the 5,10 diol. The mother liquors upon standing gave a smaller second crop of material which was filtered, washed, and dried to give a second crop of crystals. The NMR showed this material to be the 10-hydroxy-estra-4-ene-3,17-dione (III) by the presence of the olefinic H at C-4; 5.79 ppm (1H, d, J=1.6 hz).

Example 19 estra-4,9(10)-diene-3,17-dione (V)

A mixture of the products (III) and (IV) from example 18 (210.3 Mmoles) was slurried in 130 ml of dichloromethane and added over 30 minutes to a mixture of 103 ml of 96% sulfuric acid and 1.7 ml of 85% phosphoric acid which had been precooled to 2° C. The reaction was complete 90 minutes after the addition was finished. The mixture was added to 200 grams of ice and 100 ml of water; this was extracted with several portions of dichloromethane. The organic phase was concentrated to about 100 ml and 400 ml of isopropyl alcohol was added. This solution was concentrated to about 300 ml volume and cooled slowly to −20° C. The crystalline mass was filtered, washed with 2×30 ml of cold isopropanol and dried to give the product. The m.p. was 138.6–139.0° C., and the optical rotation [α]D=−132.5° (Cl, chloroform). NMR (CDCl₃); 1.02 ppm (3H, s), 1.3–3.0 ppm, several multiplets, 5.70 ppm (1H, s).

Example 20

Estra-4,9(10)-diene-3,17-dione (V)

Estra-5(10),9(11)-diene-3,17-dione (VI $R_1=R_2=R_3=H$) 0.52 g was dissolved in 2 ml of methylene chloride and 1 ml of 85% phosphoric acid was added. The two phase solution was vigorously stirred for ½ hour. The upper methylene chloride phase was decanted, water was added to the darker lower phase resulting in precipitation of the product. Silica gel thin layer chromatography showed very clean estra-4,9 (10)diene product (V) ($R_1=R_2=R_3=H$).

What is claimed is:
1. Compound of formula (IIA):

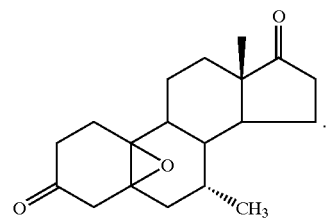

IIA

2. Compounds of formula (III):

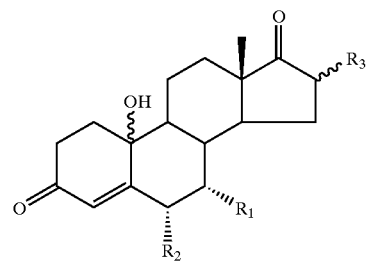

III where $R_1$ is selected from $CH_3$ and $COOCH_3$; $R_2$ is selected from $CH_3$, F, and H; and $R_3$ is selected from $CH_3$, OH, F, and H.

3. Compounds of claim 2 where $R_1 = CH_3$, $R_2 = R_3 = H$.

4. Compounds of formula (IV):

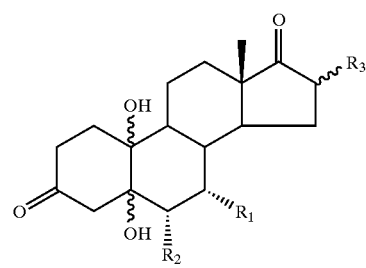

IV where $R_1$ is selected from $CH_3$ and $COOCH_3$; $R_2$ is selected from $CH_3$, F, and H; and $R_3$ is selected from $CH_3$, OH, F, and H.

5. Compounds of claim 4 where $R_1 = CH_3$, $R_2 = R_3 = H$.

* * * * *